(12) United States Patent
Barker

(10) Patent No.: US 7,941,227 B2
(45) Date of Patent: May 10, 2011

(54) IMPLANTABLE ELECTRIC STIMULATION SYSTEM AND METHODS OF MAKING AND USING

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 181 days.

(21) Appl. No.: 12/203,674

(22) Filed: Sep. 3, 2008

(65) Prior Publication Data

US 2010/0057176 A1    Mar. 4, 2010

(51) Int. Cl.
*A61N 1/00* (2006.01)
(52) U.S. Cl. ........................................................ 607/117
(58) Field of Classification Search .................. 607/116, 607/117
See application file for complete search history.

(56) References Cited

U.S. PATENT DOCUMENTS

| | | |
|---|---|---|
| 4,141,365 A | 2/1979 | Fischell et al. |
| 5,158,097 A | 10/1992 | Christlieb |
| 5,241,957 A | 9/1993 | Camps et al. |
| 5,443,492 A | 8/1995 | Stokes et al. |
| 5,562,722 A | 10/1996 | Racz et al. |
| 6,002,964 A | 12/1999 | Feler et al. |
| 6,104,957 A | 8/2000 | Alo et al. |
| 6,181,969 B1 | 1/2001 | Gord |
| 6,216,045 B1 | 4/2001 | Black et al. |
| 6,240,316 B1 | 5/2001 | Richmond et al. |
| 6,308,103 B1 | 10/2001 | Gielen et al. |
| 6,356,786 B1 | 3/2002 | Rezai et al. |
| 6,356,787 B1 | 3/2002 | Rezai et al. |
| 6,438,423 B1 | 8/2002 | Rezai et al. |
| 6,516,227 B1 | 2/2003 | Meadows et al. |
| 6,574,512 B1 | 6/2003 | Zhang et al. |
| 6,606,521 B2 * | 8/2003 | Paspa et al. ................... 607/116 |
| 6,609,029 B1 | 8/2003 | Mann et al. |
| 6,609,032 B1 | 8/2003 | Woods et al. |
| 6,671,544 B2 | 12/2003 | Baudino |
| 6,725,096 B2 | 4/2004 | Chinn et al. |
| 6,741,892 B1 | 5/2004 | Meadows et al. |

(Continued)

FOREIGN PATENT DOCUMENTS

EP    1303332 B1    12/2004

(Continued)

OTHER PUBLICATIONS

U.S. Appl. No. 11/379,707, filed Apr. 21, 2006.

(Continued)

*Primary Examiner* — George Manuel
(74) *Attorney, Agent, or Firm* — Frommer Lawrence & Haug LLP; Patrick R. Turner

(57) ABSTRACT

An insertion kit includes a lead and a splitable member configured and arranged for receiving the lead when implanting the lead into a patient. The lead has a distal end and at least two proximal ends. The lead includes a plurality of electrodes disposed at the distal end, a plurality of terminals disposed at the proximal ends, and a plurality of conductive wires coupling the plurality of electrodes electrically to the plurality of terminals. The lead also includes a junction coupling the distal end of the lead to the proximal ends of the lead. The splitable member defines a lumen for receiving the distal end of the lead and is configured and arranged to divide into at least two parts for removal of the splitable member from the lead upon implantation of the lead into the patient.

20 Claims, 14 Drawing Sheets

U.S. PATENT DOCUMENTS

| | | |
|---|---|---|
| 6,754,539 B1 | 6/2004 | Erickson et al. |
| 6,829,508 B2 | 12/2004 | Schulman et al. |
| 6,885,888 B2 | 4/2005 | Rezai |
| 6,950,709 B2 | 9/2005 | Baudino |
| 7,014,626 B2 | 3/2006 | Sanderson |
| 7,244,150 B1 | 7/2007 | Brase et al. |
| 7,337,003 B2 | 2/2008 | Malinowski |
| 7,359,755 B2 | 4/2008 | Jones et al. |
| 7,395,659 B2 | 7/2008 | Pott et al. |
| 7,418,292 B2 | 8/2008 | Shafer |
| 2002/0116030 A1 | 8/2002 | Rezai |
| 2003/0014080 A1 | 1/2003 | Baudino |
| 2003/0114905 A1 | 6/2003 | Kuzma |
| 2003/0195600 A1 | 10/2003 | Tronnes et al. |
| 2003/0220678 A1 | 11/2003 | Tronnes et al. |
| 2004/0059392 A1 | 3/2004 | Parramon et al. |
| 2004/0078070 A1 | 4/2004 | Baudino |
| 2004/0111139 A1 | 6/2004 | McCreery |
| 2004/0186545 A1 | 9/2004 | Rosero et al. |
| 2005/0004639 A1 | 1/2005 | Erickson |
| 2005/0010262 A1 | 1/2005 | Rezai et al. |
| 2005/0033393 A1 | 2/2005 | Daglow |
| 2005/0065574 A1 | 3/2005 | Rezai |
| 2005/0075701 A1 | 4/2005 | Shafer |
| 2005/0075702 A1 | 4/2005 | Shafer |
| 2005/0080325 A1 | 4/2005 | Erickson |
| 2005/0159799 A1 | 7/2005 | Daglow et al. |
| 2005/0165465 A1 | 7/2005 | Pianca et al. |
| 2005/0177201 A1 | 8/2005 | Freeman |
| 2005/0283200 A1 | 12/2005 | Rezai et al. |
| 2005/0283201 A1 | 12/2005 | Machado et al. |
| 2005/0288758 A1 | 12/2005 | Jones et al. |
| 2005/0288759 A1 | 12/2005 | Jones et al. |
| 2005/0288760 A1 | 12/2005 | Machado et al. |
| 2006/0030204 A1 | 2/2006 | Jones et al. |
| 2006/0058597 A1 | 3/2006 | Machado et al. |
| 2006/0085046 A1 | 4/2006 | Rezai et al. |
| 2006/0100667 A1 | 5/2006 | Machado et al. |
| 2006/0111754 A1 | 5/2006 | Rezai et al. |
| 2006/0156710 A1 | 7/2006 | Pott |
| 2006/0195159 A1 | 8/2006 | Bradley et al. |
| 2006/0200200 A1 | 9/2006 | Malinowski et al. |
| 2006/0287678 A1 | 12/2006 | Shafer |
| 2007/0142863 A1 | 6/2007 | Bradley |
| 2007/0150007 A1 | 6/2007 | Anderson et al. |
| 2007/0168007 A1 | 7/2007 | Kuzma et al. |
| 2007/0219595 A1 | 9/2007 | He |
| 2007/0239243 A1 | 10/2007 | Moffitt et al. |
| 2007/0239246 A1 | 10/2007 | Camps et al. |
| 2007/0239247 A1 | 10/2007 | Camps et al. |
| 2007/0255365 A1 | 11/2007 | Gerber et al. |
| 2007/0255366 A1 | 11/2007 | Gerber et al. |
| 2007/0255383 A1 | 11/2007 | Gerber et al. |
| 2008/0071320 A1 | 3/2008 | Brase |
| 2008/0188916 A1 | 8/2008 | Jones et al. |
| 2008/0255646 A1 | 10/2008 | Benabid et al. |

FOREIGN PATENT DOCUMENTS

| | | |
|---|---|---|
| WO | WO-03/002194 A2 | 1/2003 |
| WO | WO-03/002194 B1 | 1/2003 |
| WO | WO-03/041559 A2 | 5/2003 |
| WO | WO-03/066154 A2 | 8/2003 |
| WO | WO-2004/052176 A2 | 6/2004 |
| WO | WO-2005/016447 A2 | 2/2005 |
| WO | WO-2005/107854 A2 | 11/2005 |
| WO | WO-2005/107859 A1 | 11/2005 |
| WO | WO-2006/007048 A2 | 1/2006 |
| WO | WO-2006/031899 A2 | 3/2006 |
| WO | WO-2006/119135 A2 | 11/2006 |
| WO | WO-2007/114998 A1 | 10/2007 |
| WO | WO-2007/115158 A2 | 10/2007 |

OTHER PUBLICATIONS

U.S. Appl. No. 11/238,240 filed Sep. 29, 2005.
International Search Report PCT/US2009/054897; mailed May 18, 2010.

* cited by examiner

IMPLANTABLE ELECTRIC STIMULATION SYSTEM AND METHODS OF MAKING AND USING

TECHNICAL FIELD

The present invention is directed to the area of implantable electrical stimulation systems and methods of making and using the systems. The present invention is also directed to implantable electrical stimulation systems that include a lead with an increased number of electrodes disposed on a distal end of the lead without a corresponding increase in the lateral circumference of the distal end of the lead and the lead also including multiple proximal ends, as well as methods of making and implanting the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an insertion kit includes a lead and a splitable member configured and arranged for receiving the lead when implanting the lead into a patient. The lead has a distal end and at least two proximal ends. The lead includes a plurality of electrodes disposed at the distal end, a plurality of terminals disposed at the proximal ends, and a plurality of conductive wires coupling the plurality of electrodes electrically to the plurality of terminals. The lead also includes a junction coupling the distal end of the lead to the proximal ends of the lead. The splitable member defines a lumen for receiving the distal end of the lead and is configured and arranged to divide into at least two parts for removal of the splitable member from the lead upon implantation of the lead into the patient.

In another embodiment, an electrical stimulating system includes a lead, a splitable member, a control module, and a connector. The lead has a distal end and at least two proximal ends. The lead includes a plurality of electrodes disposed at the distal end, a plurality of terminals disposed at the proximal ends, and a plurality of conductive wires coupling a portion of the plurality of electrodes electrically to the plurality of terminals. The lead also includes a junction coupling the distal end of the lead to the proximal ends of the lead. The splitable member is configured and arranged for receiving the lead when implanting the lead into a patient. The splitable member defines a lumen for receiving the distal end of the lead and is configured and arranged to divide into at least two parts for removal of the splitable member from the lead upon implantation of the lead into the patient. The control module is configured and arranged to electrically couple to the first proximal end and the at least one second proximal end. The control module includes a housing and an electronic subassembly disposed in the housing. The connector receives the lead and includes a connector housing and a plurality of connector contacts disposed in the connector housing. The connector housing defines a first port for receiving the first proximal end and at least one second port for receiving the at least one second proximal end of the lead. The connector contacts are configured and arranged to couple to at least one first terminal disposed at the first proximal end of the lead and to at least one second terminal disposed at each of the at the at least one second proximal ends.

In yet another embodiment, a neurostimulation lead includes a distal lead body, at least two proximal lead bodies, and a junction coupling the distal lead body to the at least two proximal lead bodies. The distal lead body includes a distal end and a proximal end. The distal lead body includes a plurality of electrodes disposed on the distal end, a plurality of conductive wires extending from the electrodes to the proximal end, and a plurality of lumens extending from the electrodes to the proximal end. Each of the plurality of lumens is configured and arranged for receiving a plurality of the conductive wires. The at least two proximal lead bodies include a distal end and a proximal end. The at least two proximal lead bodies each include a plurality of terminals disposed on the proximal end, a plurality of conductive wires extending from the terminals to the distal end, and a plurality of lumens extending from the terminals to the distal end. Each of the plurality of lumens is configured and arranged for receiving a single conductive wire. The junction couples the proximal end of the distal lead body to the distal ends of each of the proximal lead bodies. Each of the conductive wires extending from the electrodes electrically couples to at least one conductive wire extending from at least one of the terminals disposed on at least one of the proximal lead bodies.

In still yet another embodiment, a method for implanting a lead into a patient includes inserting an obturator into a splitable member that defines a lumen for receiving the obturator and guiding the splitable member with the obturator to a desired location within the patient. The method also includes removing the obturator, leaving the splitable member in the patient, and inserting into the lumen of the splitable member a distal end of a lead. The lead includes a plurality of electrodes disposed along the distal end of the lead and a plurality of terminals disposed along at least one proximal end of the lead. The method further includes separating the splitable member into at least two parts along the length of the lumen and removing the splitable member from the lead, leaving at least the distal end of the lead implanted in the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a lead with an increased number of electrodes disposed on a distal end of the lead without a corresponding increase in the lateral circumference of the distal end of the lead and the lead also including multiple proximal ends, as well as methods of making and implanting the leads and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
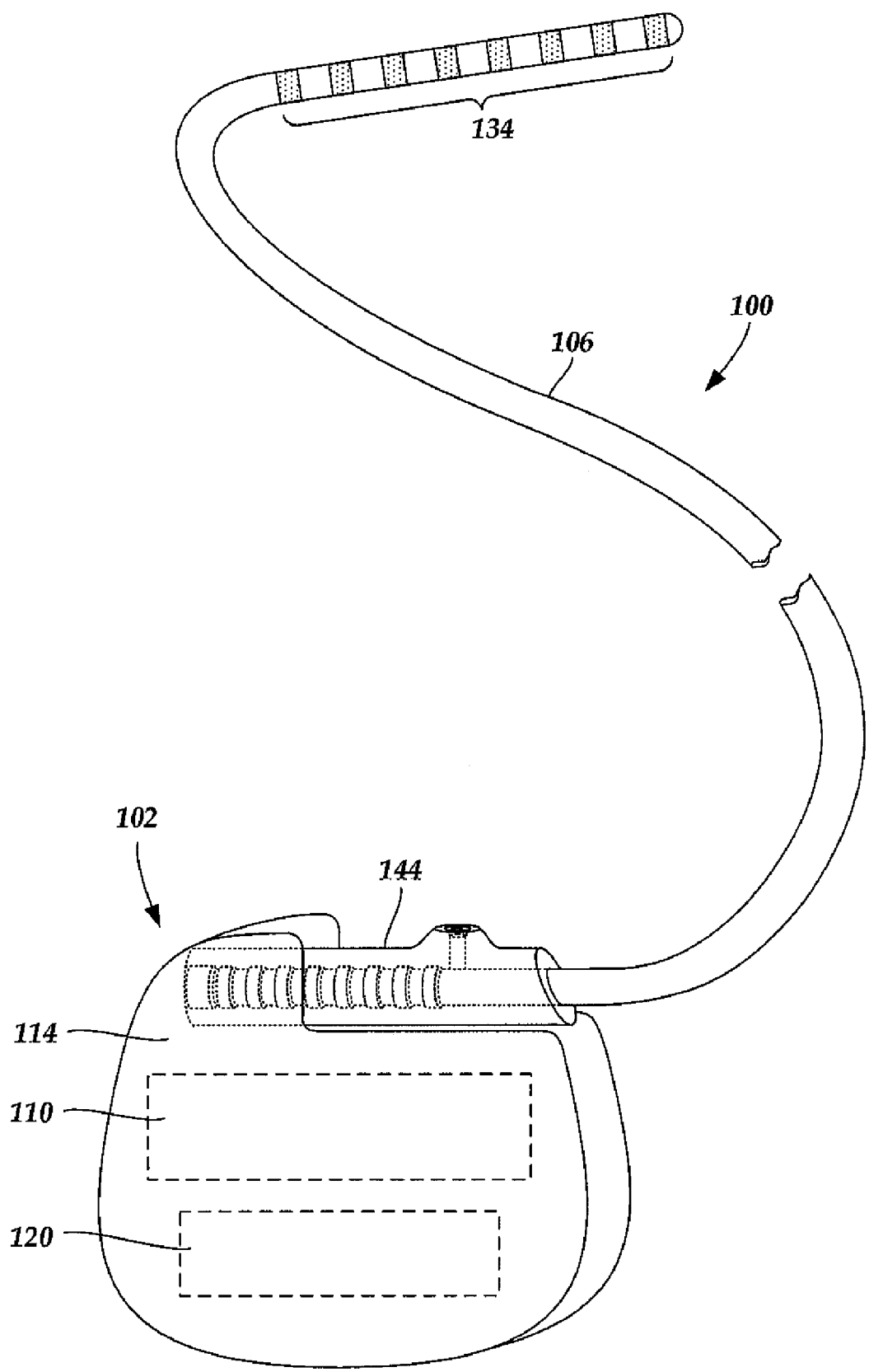
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead body 106 ("lead") coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead body 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 213) is only connected to one electrode 134. The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment the one or more lumens may be flushed continually, or on a regular basis, with saline, epidural fluid, or the like. In at least some embodiments, the one or more lumens can be permanently or removably sealable at the distal end.

Figure 2A:
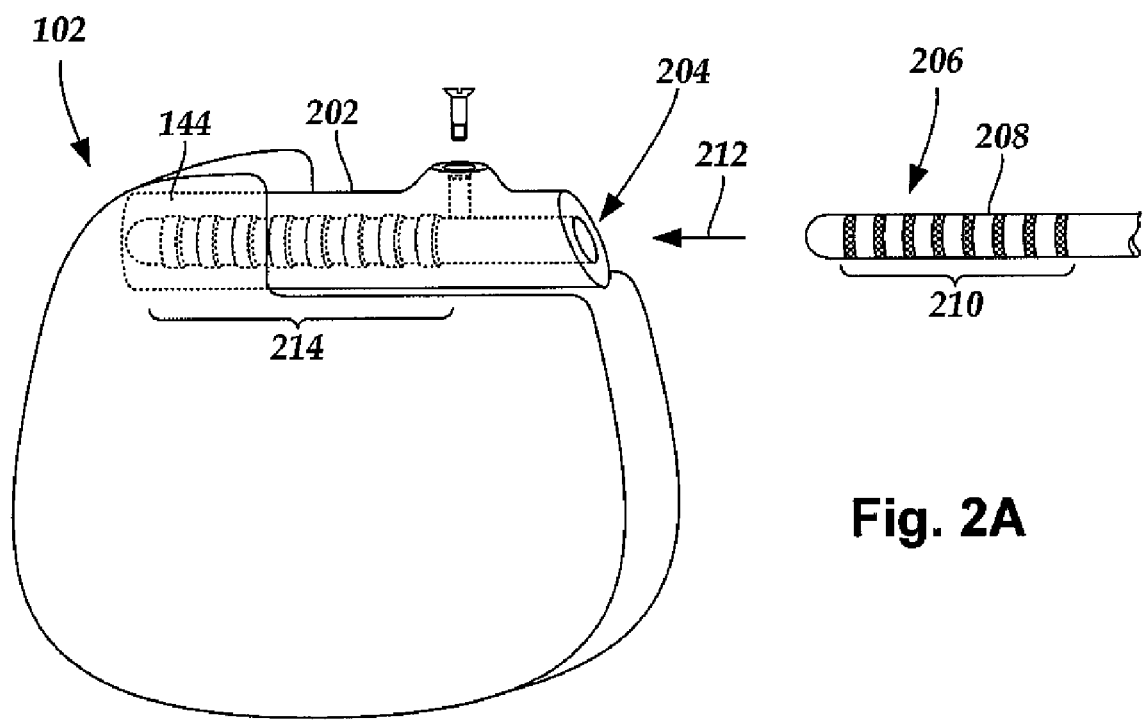
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. No. 7,244,150 and U.S. patent application Ser. No. 11/532,844, which are incorporated by reference.

Figure 2B:
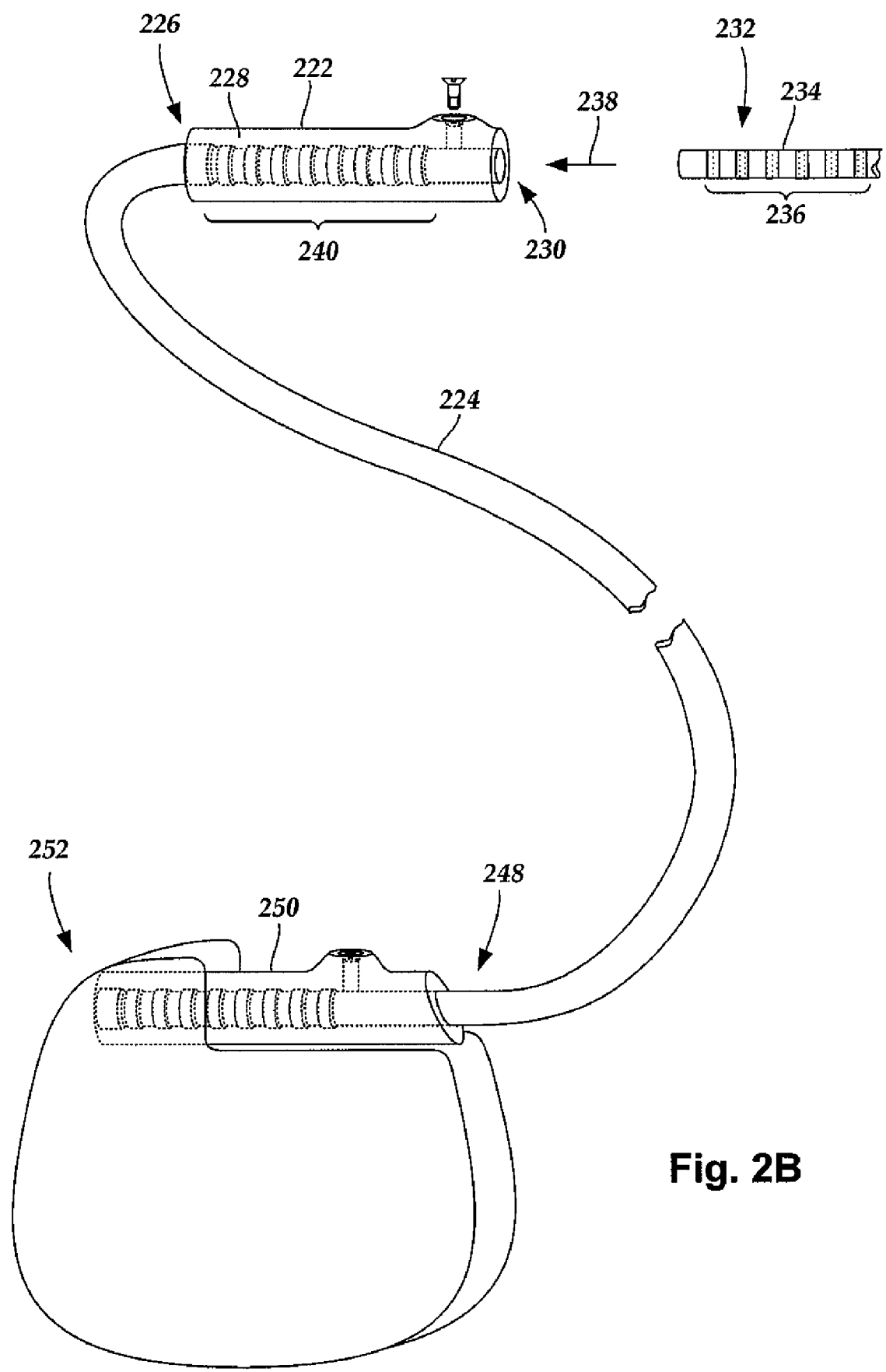
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 213 the proximal end 248 of the lead extension 224 is inserted into a connector 250 disposed in a control module 252.

Sometimes a patient may be experiencing pain emanating from an area greater in length than the length of an array of electrodes (e.g., 134 of FIGS. 1 and 2) disposed on the distal end of a lead. For example, a patient may experience pain in an area spanning multiple vertebral bodies. One way to increase stimulation coverage is to provide a lead with a greater length and either increase the amount of space between adjacent electrodes, or increase the size of one or more of the electrodes. However, when the amount of space between adjacent electrodes is increased or the size of one or more of the electrodes in increased, linear electrode density may decrease to a sub-therapeutic level.

Another way to increase stimulation coverage is to provide a lead with a greater length and increase the number of electrodes on the lead. However, a lead with additional electrodes may also need an increased number of conductive wires to electrically couple the electrodes to a control module. When an increased number of conductive wires are utilized in a lead, the lead may become incompatible with existing control modules. For example, the lateral circumference of the lead may too large to mate with a connector of a control module, or the number of terminals disposed on the lead may exceed the number of corresponding connective contacts disposed in the control module. One option for facilitating compatibility between a lead and a control module is to couple a proximal end of the lead to a lead adaptor that splits the conductive wires at the proximal end of the lead into two or more groupings of conductive wires that each couple with a control module.

In at least some embodiments, stimulation coverage is increased by increasing the number of electrodes disposed at the distal end of a lead, preferably without increasing the lateral circumference of a distal end of the lead and without using a lead adaptor to divide conductive wires. In at least some embodiments, a lead includes a junction coupling the distal end of the lead with two or more proximal ends. Conductive wires disposed in the distal end of the lead are split at the junction into two or more groupings of conductive wires. Each grouping of conductive wires is disposed in a different proximal end. Each proximal end is configured and arranged to electrically couple at least one of the conductive wires disposed in the proximal end to at least one conductive contact disposed in a connector of a control module.

Figure 3:
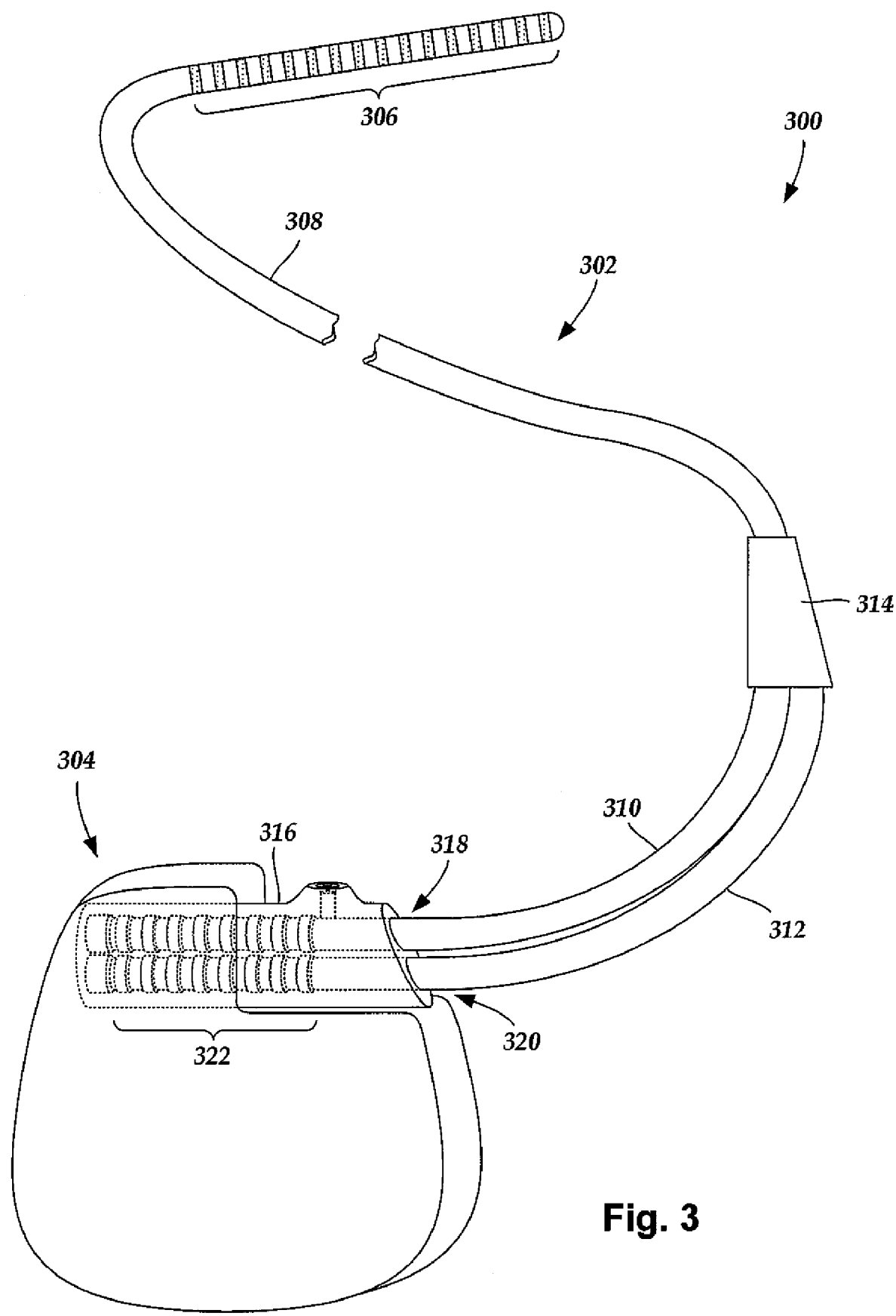
FIG. 3 is a schematic view of one embodiment of an electrical stimulation system with a lead that includes multiple proximal ends coupled to a control module, according to the invention.

In at least some embodiments, each proximal end is coupled to a single connector of a single control module. FIG. 3 is a schematic view of one embodiment of an electrical stimulation system 300 that includes a lead 302 and a control module 304. The lead 302 includes a plurality of electrodes 306 disposed at a distal end 308 and a plurality of terminals (see e.g., 714 and 716 in FIG. 7) disposed on each of a plurality of proximal ends 310 and 312. A junction 314 couples the distal end 308 to the plurality of proximal ends 310 and 312. The junction 314 can be made using any non-conductive material suitable for implantation including, for example, silicone, polyurethane, PEEK, epoxy, and the like or combinations thereof. In at least some embodiments, the junction 314 may also provide mechanical sealing of any conductive wires disposed within the junction 314 to ameliorate current leakage.

In FIG. 3 and in other figures, two proximal ends are shown as a representation of a plurality of proximal ends for clarity of illustration. The plurality of proximal ends includes a first proximal end and one or more second proximal ends. In FIG. 3, the plurality of proximal ends includes a first proximal end 310 and a second proximal end 312. In a preferred embodiment, at least one of the proximal ends is a continuation of a distal end and any other proximal end(s) terminate(s) at the junction. For example, in FIG. 3 the first proximal end 310 is a continuation of the distal end 308 and the second proximal end 310 terminates at the junction 314. In some embodiments, the lead can include more than two proximal ends. For example, there can be one, two, three, four, five, six, seven, eight, nine, ten, twelve, fourteen, sixteen, or more proximal ends. As will be recognized, other numbers of proximal ends may also be used.

The control module 304 includes a connector 316 that defines a plurality of ports 318 and 320 configured and arranged to receive the first proximal end 310 and the second proximal 312. In a preferred embodiment, the number of ports is equal to the number of proximal ends of the lead 302. A plurality of conductor contacts 322 are disposed in each of the ports 318 and 320 and are configured and arranged to electrically couple the control module 304 to the electrodes 306. In at least some embodiments, conductive wires are routed to either the first proximal end 310 or the second proximal end 312 at the junction 314. In at least some embodiments, the length of the distal end 308 is substantially greater than the length of the first proximal end 310 and the second proximal end 312. In at least some embodiments, the first proximal end 310 and the second proximal end 312 are also configured and arranged to couple with other devices, such as lead extensions, adaptors, operating room cables, and the like or combinations thereof. In FIG. 3, the ports 318 and 320 are shown arranged vertically on the control module 304. In alternate embodiments, the ports 318 and 320 are arranged in other orientations, such as side-by-side, or on different sides of the control module 304.

In a preferred embodiment, the number of conductive wires disposed in the first proximal end 310 is approximately equal to the number of conductive wires disposed in the second proximal end 312. In one exemplary embodiment, the lead 302 includes sixteen electrodes 306 electrically coupled with eight terminals (see e.g., 714 in FIG. 7) disposed on the first proximal end 310 and eight terminals (see e.g., 716 in FIG. 7) disposed on the second proximal end 312. Accordingly, in one embodiment, sixteen conductive wires are disposed in the distal end 308 of the lead 302 and are split into two groupings of eight conductive wires each at the junction 314. Eight conductive wires are disposed in the first proximal end 310 and eight conductive wires are disposed in the proximal end 312. The corresponding connector 316 includes sixteen conductor contacts 322 configured and arranged with eight conductor contacts 322 disposed in each of the two ports 318 and 320 to electrically couple with the eight terminals disposed on each of the first proximal end 310 and the second proximal end 312 when the first proximal end 310 and the second proximal end 312 are inserted into the ports 318 and 320, respectively.

Figure 4:
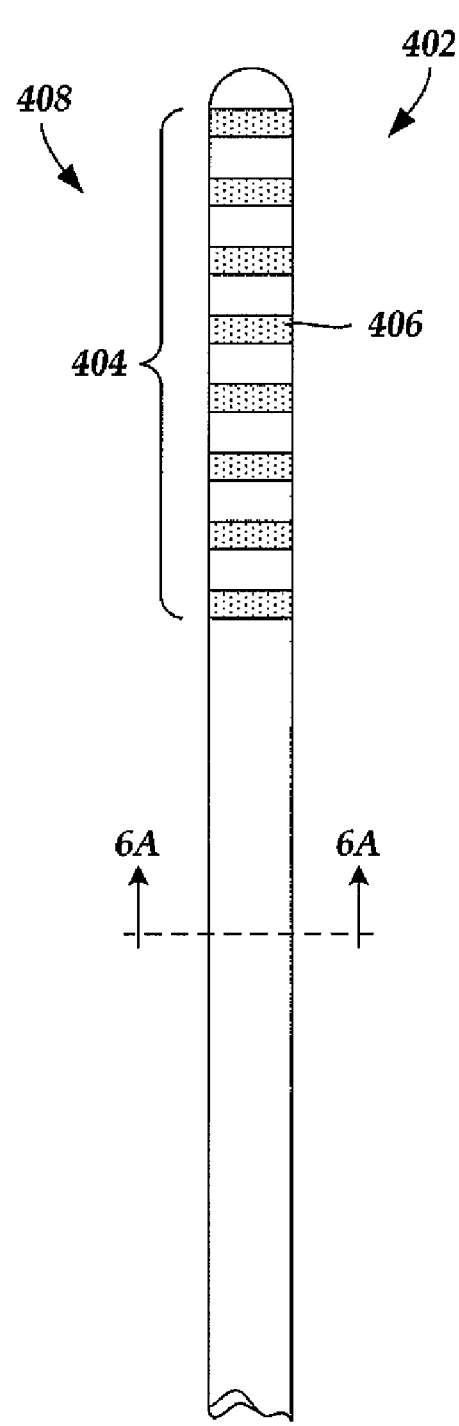
FIG. 4 is a schematic side view of one embodiment of a portion of a distal end of a conventional lead of an electrical stimulation system, according to the invention.

FIG. 4 is a schematic side view of one embodiment of a portion of a distal end of an exemplary conventional lead 402. The exemplary conventional lead 402 includes a plurality of electrodes 404, such as electrode 406, disposed on a distal end 408 of the exemplary conventional lead 402. Additional features of the exemplary conventional lead 402 are described below, with respect to FIG. 6A, for comparison with at least some embodiments.

Figure 5:
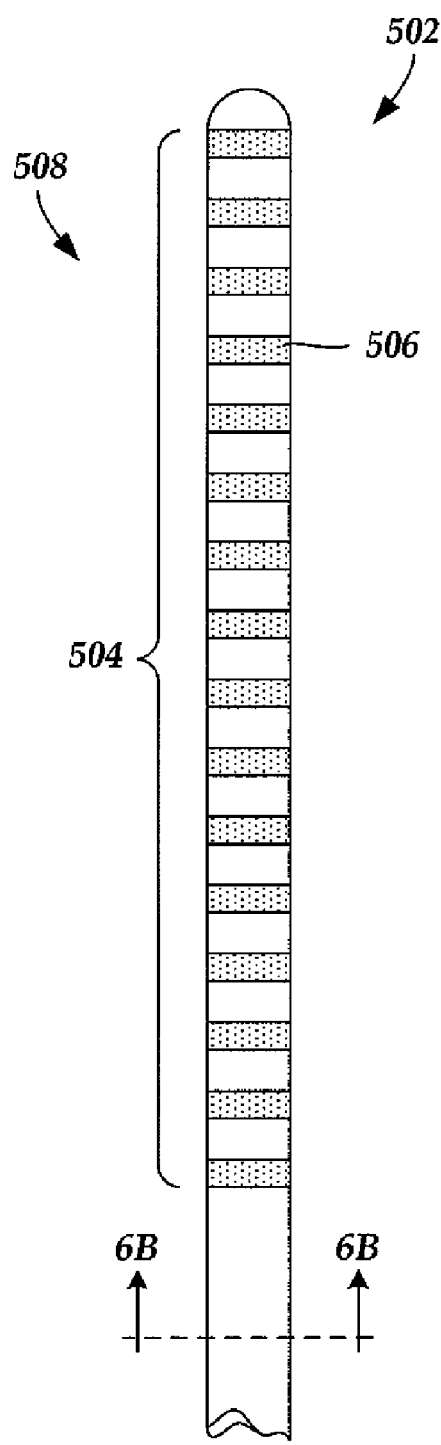
FIG. 5 is a schematic side view of another embodiment of a portion of a distal end of a lead of an electrical stimulation system, according to the invention.

FIG. 5 is a schematic side view of one embodiment of a portion of a distal end of a lead 502 with a lateral circumference that is equal to the lateral circumference of the exemplary conventional lead 402, but that includes twice the number of electrodes from the exemplary conventional lead 402. The lead 502 includes a plurality of electrodes 504, such as electrode 506, disposed on a distal end 508 of the lead 502. The plurality of electrodes 504 is greater than the plurality of electrodes 404 in FIG. 4 without a corresponding increase in the lateral circumference of the lead 502. In a preferred embodiment, the number of electrodes disposed on the lead 502 is twice the number of electrodes disposed on the exemplary conventional lead 402. For example, in FIG. 4, eight electrodes are shown on the exemplary conventional lead 402, while in FIG. 5 sixteen electrodes are shown on the lead 502. In one embodiment, the portion of the lead 502 distal to the junction (314 in FIG. 3) is isodiametric. In one particular embodiment, the lead 502 has a lateral nominal diameter of 0.053 inches (0.135 cm).

Figure 6A:
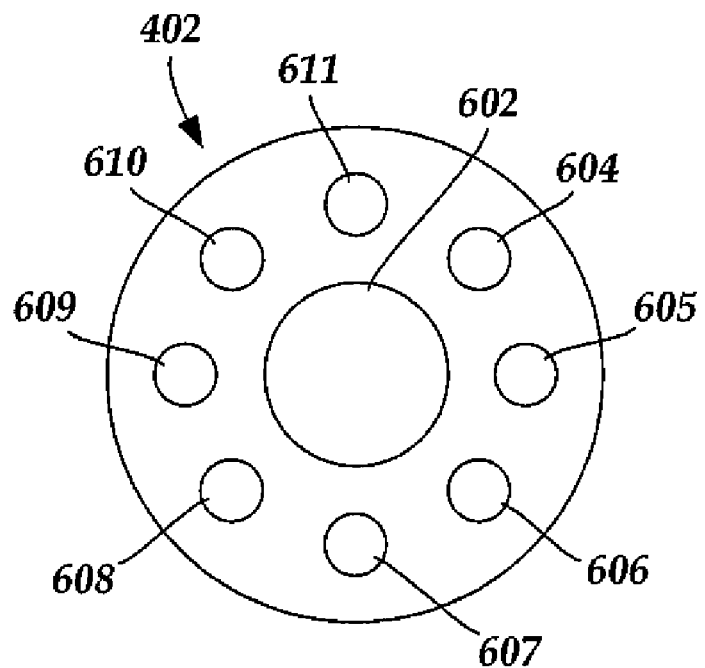
FIG. 6A is a schematic transverse cross-sectional view of one embodiment of the distal end of the lead shown in FIG. 4, according to the invention.

Conductive wires may be used to electrically couple electrodes on a distal end of a lead to terminals on a proximal end of a lead. As discussed above, with reference to FIG. 1, conductive wires may be embedded in the non-conductive material of the lead or can be disposed in one or more lumens extending along the lead. In some embodiments, each individual conductive wire is disposed in an individual lumen. FIG. 6A is a schematic transverse cross-sectional view of the distal end of the exemplary conventional lead 402 shown in FIG. 4. In FIG. 6A, the exemplary conventional lead 402 includes a center lumen 602 and a plurality of outer lumens 604-611. Each outer lumen 604-611 is configured and arranged for an individual conductive wire to extend along the length of each individual outer lumen 604-611. In FIG. 6A, eight circular-shaped outer lumens 604-611 are shown. Thus, in the exemplary conventional lead 402 shown in FIG. 4, eight connector wires can be disposed in the outer lumens 604-611 and electrically coupled to eight electrodes.

Figure 6B:
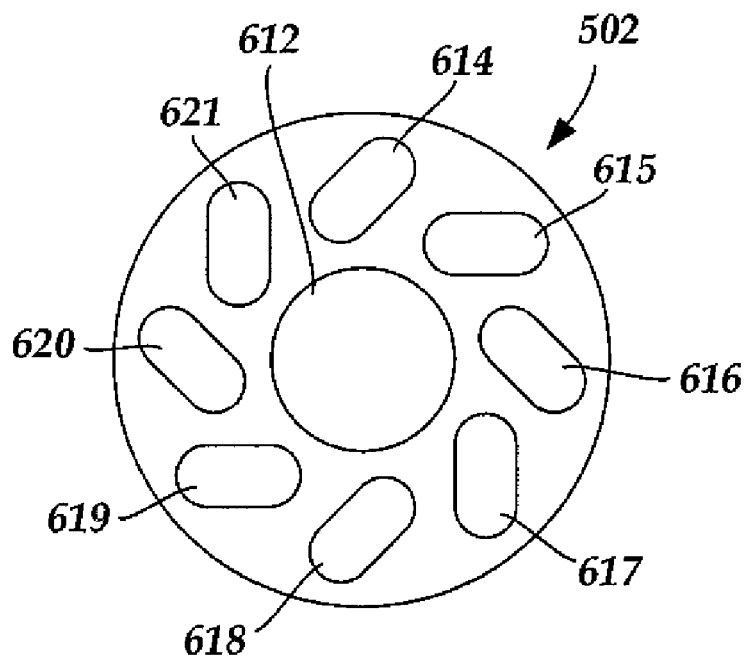
FIG. 6B is a schematic transverse cross-sectional view of one embodiment of the distal end of the lead shown in FIG. 5, according to the invention.

FIG. 6B is a schematic transverse cross-sectional view of one embodiment of the distal end of the lead 502. In FIG. 6B, the lead 502 includes a center lumen 612 and a plurality of outer lumens 614-621. Each outer lumen 614-621 is configured and arranged for multiple conductive wires to extend along the length of each individual outer lumen 614-621. In FIG. 6B, eight oval-shaped outer lumens 614-621 are shown, with each outer lumen 614-621 configured and arranged for two conductive wires to extend within each outer lumen 614-

621. Thus, in some embodiments, sixteen connector wires can be disposed in the outer lumens 614-621 and electrically coupled to sixteen electrodes.

In alternate embodiments, outer lumens can be configured and arranged to accommodate additional conductive wires. Accordingly, the number of multiple conductive wires that can be disposed in an outer lumen may vary. For example, there can be one, two, three, four, five, six, seven, eight, nine, ten, twelve, fourteen, sixteen, or more conductive wires disposed in an outer lumen. As will be recognized, other numbers of conductive wires may also be disposed in an outer lumen.

Figure 7:
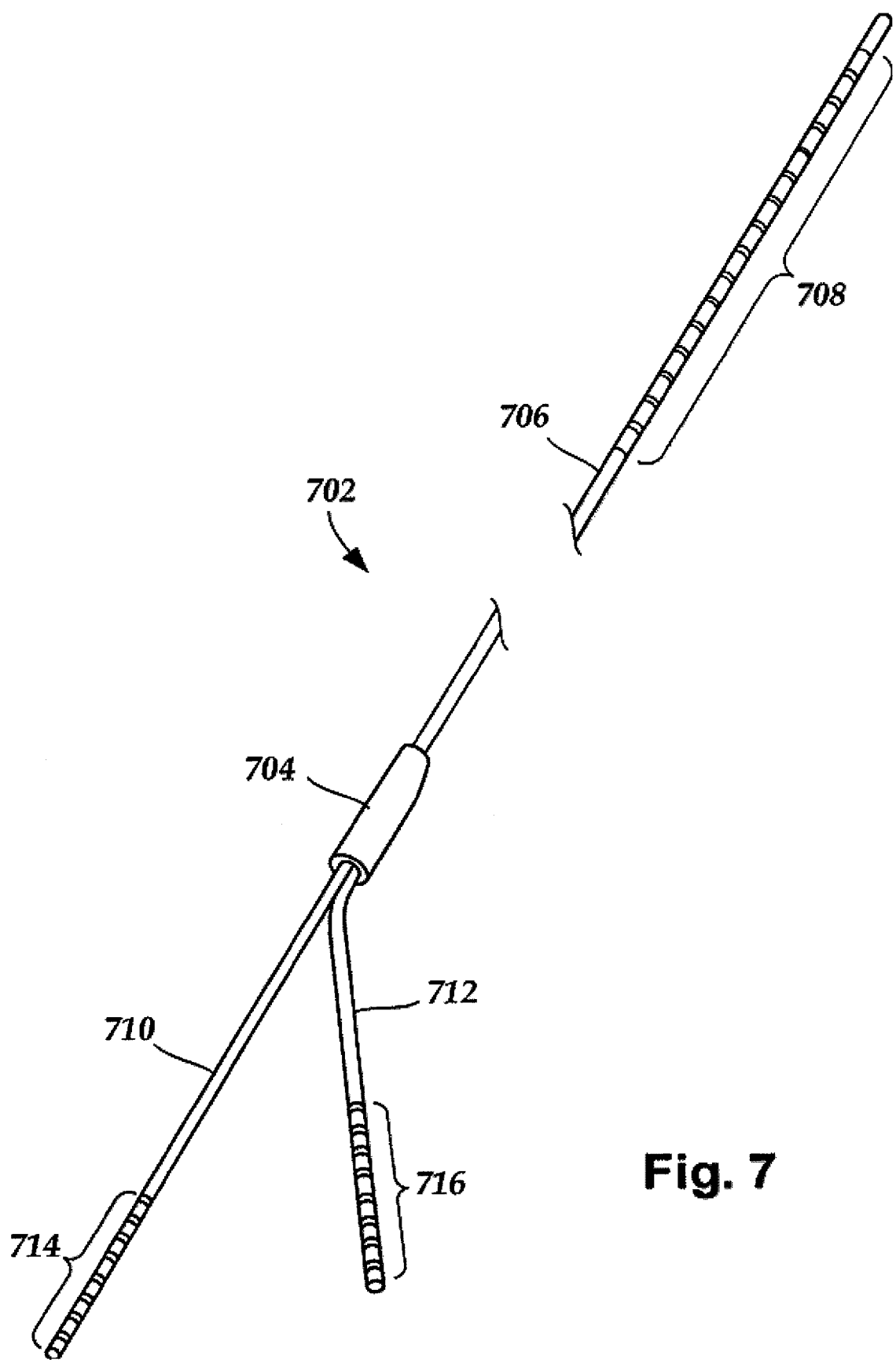
FIG. 7 is a schematic perspective view of one embodiment of a lead with a junction coupling a distal end of the lead to a plurality of proximal ends, according to the invention.

FIG. 7 is a schematic perspective view of one embodiment of a lead 702 with a junction 704 coupling a distal end 706 with electrodes 708 disposed on the distal end 706 to a first proximal end 710 and a second proximal end 712. The first proximal end 710 includes terminals 714 disposed on the first proximal end 710 and the second proximal end 712 includes terminals 716 disposed on the second proximal end 712. In at least some embodiments, the first proximal end 710 and the second proximal end 712 are each configured and arranged for insertion into one of a plurality of ports defined in a connector that is electrically coupled to a control module. In a preferred embodiment, the number of terminals 714 disposed on the first proximal end 710 is equal to the number of terminals 716 disposed on the second proximal end 712. In a preferred embodiment, the collective number of terminals 714 and 716 disposed on both the first proximal end 710 and the second proximal end 712, respectively, is equal to the number of electrodes 708 disposed on the distal end 706 of the lead 702.

Figure 8A:
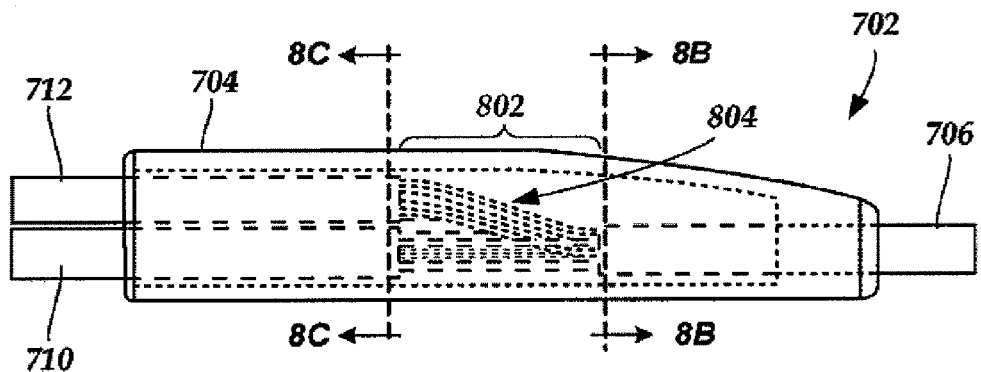
FIG. 8A is a close-up schematic side view of one embodiment of the junction of the lead shown in FIG. 7, according to the invention.

FIG. 8A is a schematic side view of one embodiment of the junction 704 disposed on the lead 702. The junction 704 couples the distal end 706 with the first proximal end 710 and the second proximal end 712. In at least some embodiments, the lateral diameter of the junction 704 is greater than the lateral diameter of the distal end 706 of the lead 702. A longitudinal schematic cross-sectional view of a conductive-wire branching region 802 is shown disposed within the junction 704. In FIG. 8A, a plurality of conductive wires 804 are shown branching from the distal end 706 to each of the first proximal end 710 and the second proximal end 712.

Figure 8B:
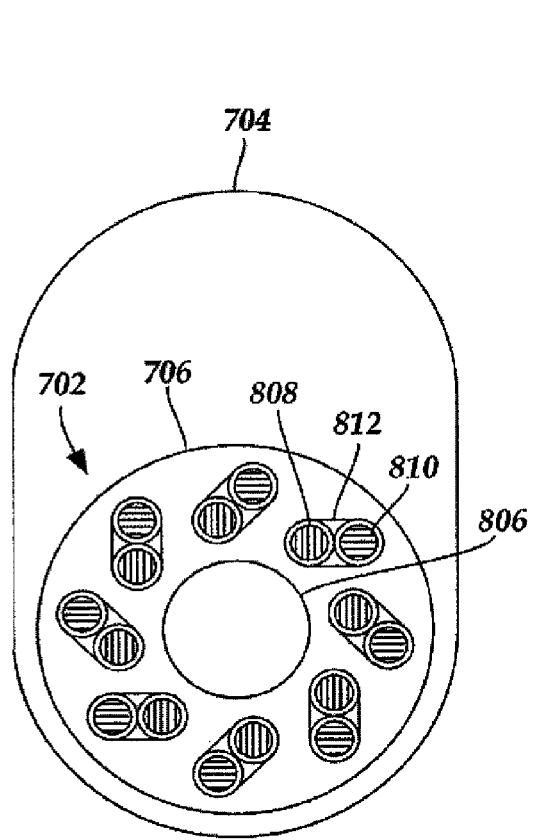
FIG. 8B is a schematic transverse cross-sectional view of one embodiment of the lead distal to the junction shown in FIG. 8A with two conductive wires disposed in each outer lumen defined in the lead, according to the invention.
Figure 8C:
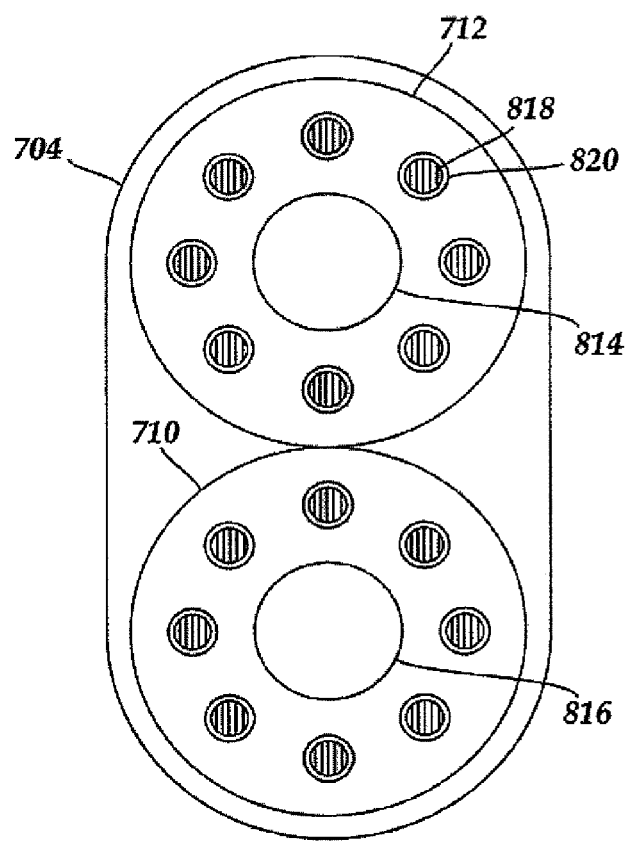
FIG. 8C is a schematic transverse cross-sectional view of one embodiment of the proximal ends proximal to the junction shown in FIG. 8A with one conductive wire disposed in each outer lumen defined in each proximal end of the lead, according to the invention.

In at least some embodiments, the number of conductive wires disposed in the distal end 806 is equal to the collective number of conductive wires disposed in both the first proximal end 808 and the second proximal end 810 and the number of conductive wires disposed in the first proximal end 808 is equal to the number of conductive wires disposed in the second proximal end 810. For example, as shown in FIGS. 8A-8C, sixteen conductive wires are shown disposed in the distal end 806 that split evenly into eight conductive wires disposed in both the first proximal end 808 and the second proximal end 810. In other embodiments, other numbers of conductive wires may be used, as well. For example, thirty-two conductive wires may be disposed in the distal end that split into a first proximal end and a second proximal end with sixteen conductive wires disposed in both the first proximal end and the second proximal end. In an alternate embodiment, thirty-two conductive wires disposed in the distal end may split into four proximal ends with eight conductive wires disposed in each of the proximal ends.

FIG. 8B is a schematic transverse cross-sectional view of one embodiment of the distal end 706 of the lead 702 disposed in the junction 704. The distal end 706 defines a central lumen 806 and a plurality of outer lumens, such as outer lumen 812. A plurality of conductive wires are disposed in each of the plurality of outer lumens, such as conductive wires 808 and 810 disposed in the outer lumen 812. Note that each of the conductive wires may be insulated to reduce the risk of short-circuiting. FIG. 8C is a schematic transverse cross-sectional view of one embodiment of the first proximal end 710 and the second proximal end 712 disposed in the junction 704. The first proximal end 710 and the second proximal end 712 each define a central lumen 814 and 816, respectively, and a plurality of outer lumens, such as outer lumen 820. An individual conductive wire is disposed in each of the plurality of outer lumens, such as the conductive wire 818 disposed in the outer lumen 820. Note that each of the conductive wires may be insulated to reduce the risk of short-circuiting between two or more conductive wires within a given lumen.

A junction may have a diameter that is greater than a distal end of a corresponding lead and may, therefore, prevent the use of conventional implantation techniques. Some conventional implantation techniques involve inserting an introducer needle, such as an epidural needle, into a patient. Once the introducer needle is inserted into the patient and positioned in a desired location, a lead is inserted into the introducer needle. Once the lead is fully inserted in the introducer sheath, the introducer needle is pulled out of the patient by sliding the introducer needle off the proximal end of the lead. A lead with one or more non-isodiametric sections, such as a lead with a junction, may prevent the sliding of the introducer needle off the proximal end of the lead. It may be particularly advantageous to be able to employ such implantation techniques during a trial stimulation, when it is especially desired to position the lead using a minimally-invasive implantation technique that may be performed in an outpatient setting.

Figure 9:
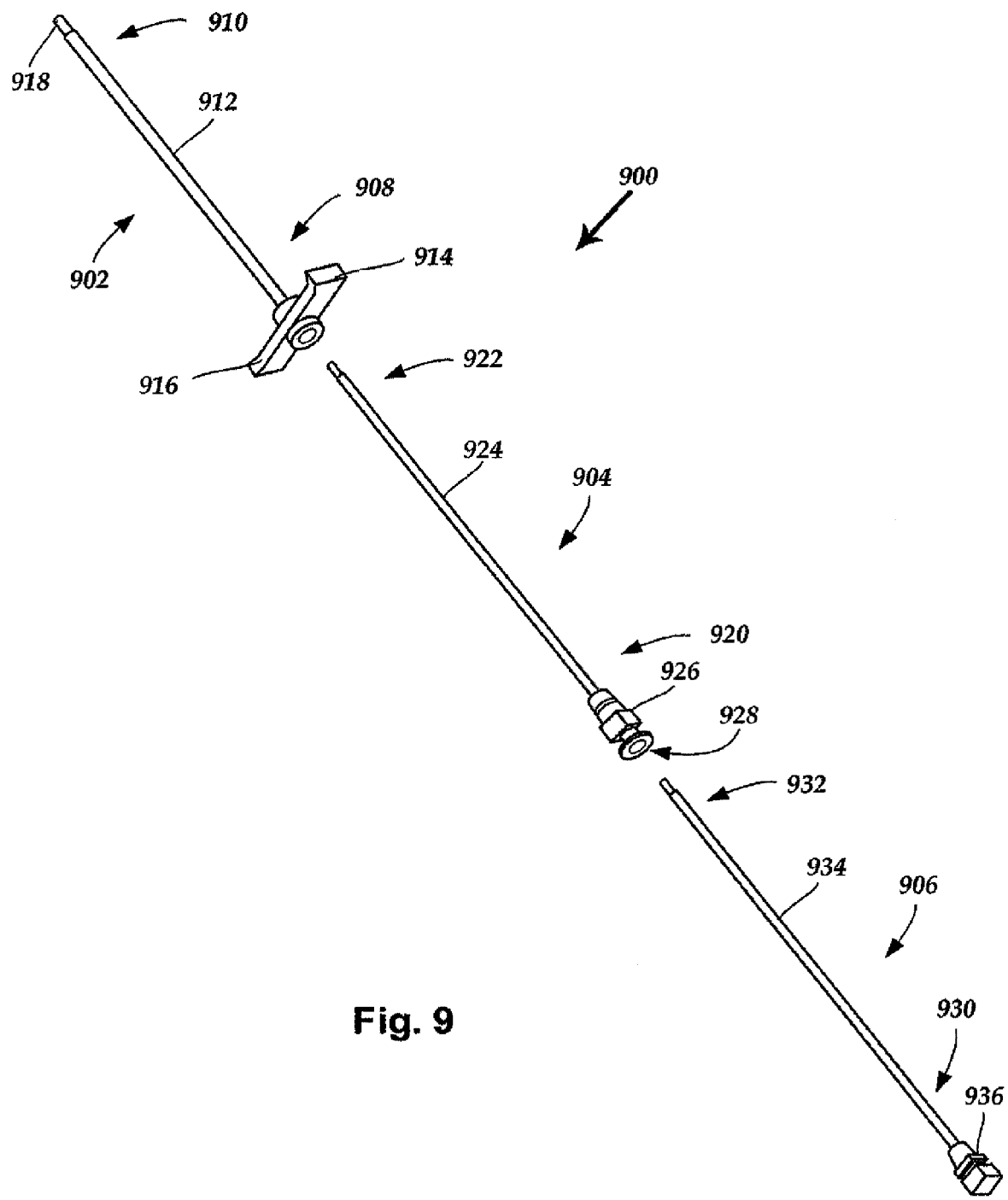
FIG. 9 is a schematic exploded perspective view of one embodiment of a pull-apart implantation system configured and arranged to facilitate implantation of an electrical stimulation system into a patient, the pull-apart implantation system including an introducer sheath, an insertion needle, and an obturator, according to the invention.

In at least some embodiments, a pull-apart implantation system can be used to facilitate implantation of an electrical stimulation system into a patient. FIG. 9 is a schematic exploded perspective view of one embodiment of a pull-apart implantation system 900. The pull-apart implantation system 900 includes an introducer sheath 902, an insertion needle 904, and an obturator 906. The introducer sheath 902 has a proximal end 908 and a distal end 910 and includes a body 912 and at least two pull-apart tabs 914 and 916 disposed at the proximal end 908. The body 912 is coupled to the pull-apart tabs 914 and 916 and includes an open tip 918 at the distal end 910 of the body 912. The body 912 includes a lumen configured and arranged to receive the insertion needle 904 and the obturator 906 or the distal end of the lead (see e.g., 702 in FIG. 7). In at least some embodiments, the junction (see e.g., 704 in FIG. 7) is too large to be insertable into the body 912.

The introducer sheath 902 is made from a flexible material suitable for implantation into a patient including, for example, fluorinated ethylene propylene, polytetrafluoroethylene, high-density polyethylene, and the like or combinations thereof. Additionally, one or more radiopaque materials may be added including, for example, barium sulfate and bismuth subcarbonate, and the like or combinations thereof to facilitate implantation of the introducer sheath through the use of one or more medical imaging techniques, such as fluoroscopy.

The insertion needle 904 can be made from a rigid material suitable for implantation, such as stainless steel, and has a proximal end 920 and a distal end 922 and may include a cannula 924 and a hub 926 disposed at the proximal end 920 of the insertion needle 904. The hub 926 may include a luer fitting 928 or other suitable arrangement configured and arranged to receive a syringe. The cannula 924 preferably has a longitudinal length that is at least as great as the body 912 of the introducer sheath 902 and configured and arranged for insertion into the body 912. When the longitudinal length of the cannula 924 is greater than the body 912, the distal end of the cannula 924 extends through the open tip 918 of the body 912. In at least some embodiments, the lateral circumference of the cannula 924 is no greater than sixteen-gauge. The cannula 924 is hollow and configured and arranged to receive the obturator 906. In at least some embodiments, the junction (see e.g., 704 in FIG. 7) is too large to be insertable into the cannula 924. The obturator 906 has a proximal end 930 and a distal end 932 and includes an insertion rod 934 and a base 936. The insertion rod 934 is configured and arranged for insertion into the cannula 924 of the insertion needle 904 and includes a blunt tip configured and arranged for preventing coring of patient tissue when the insertion needle 904 is inserted into a patient.

Figure 10:
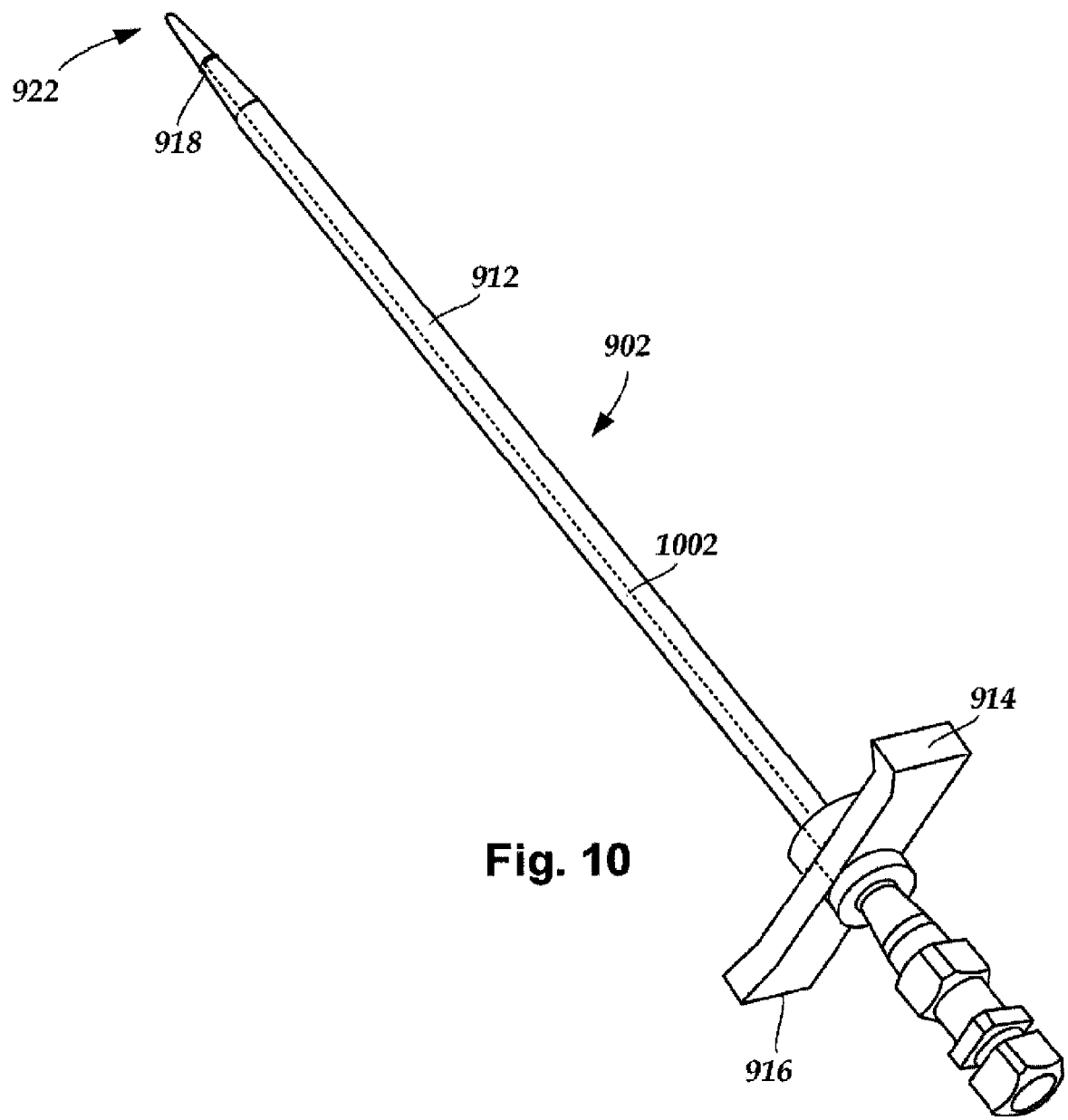
FIG. 10 is a schematic perspective view of one embodiment of the pull-apart implantation system shown in FIG. 9 with an insertion needle and an obturator inserted into an introducer sheath, according to the invention.

FIG. 10 is a schematic perspective view of one embodiment of the pull-apart implantation system 900 with the insertion rod (934 in FIG. 9) of the obturator (906 in FIG. 9) disposed in the cannula (924 in FIG. 9) of the insertion needle (904 in FIG. 9) which, in turn, is disposed in the body 912 of the introducer sheath 902. In FIG. 10, the distal end 922 of the cannula (924 in FIG. 9) is shown extending through the open tip 918 of the body 912.

The body 912 includes one or more weakened regions 1002, such as score lines or perforations, extending along at least a portion of the longitudinal length of the body 912 from between the at least two pull-apart tabs 914 and 916. In at least some embodiments, when the at least two pull-apart tabs 914 and 916 are separated from one another, for example, by pulling each pull-apart tab away from the other pull-apart tab(s) in directions approximately orthogonal to the body 912, the body 912 separates along the one or more weakened regions 1002.

Figure 11:
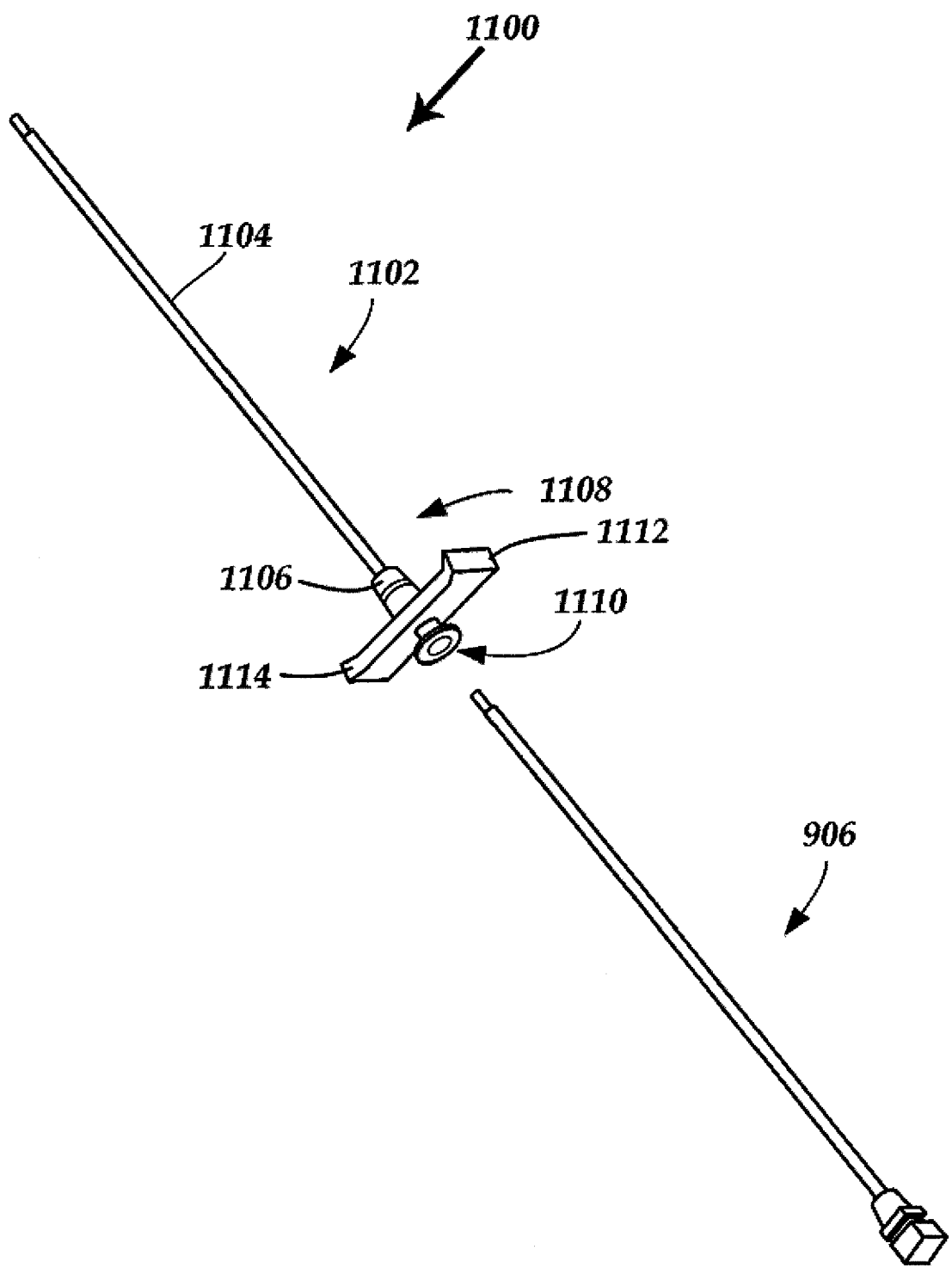
FIG. 11 is a schematic exploded perspective view of another embodiment of a pull-apart implantation system configured and arranged to facilitate implantation of an electrical stimulation system into a patient, the pull-apart implantation system including an insertion needle and an obturator, according to the invention.

FIG. 11 is a schematic exploded perspective view of another embodiment of a pull-apart implantation system 1100. The pull-apart implantation system 1100 includes an insertion needle 1102 and the obturator 906. The insertion needle 1102 includes a cannula 1104 and a hub 1106 disposed at a proximal end 1108 of the insertion needle 1102. In at least some embodiments, the hub 1106 includes a luer fitting 1110 or other suitable arrangement configured and arranged to receive a syringe. Additionally, the hub 1106 includes pull-apart tabs 1112 and 1114.

Figure 12:
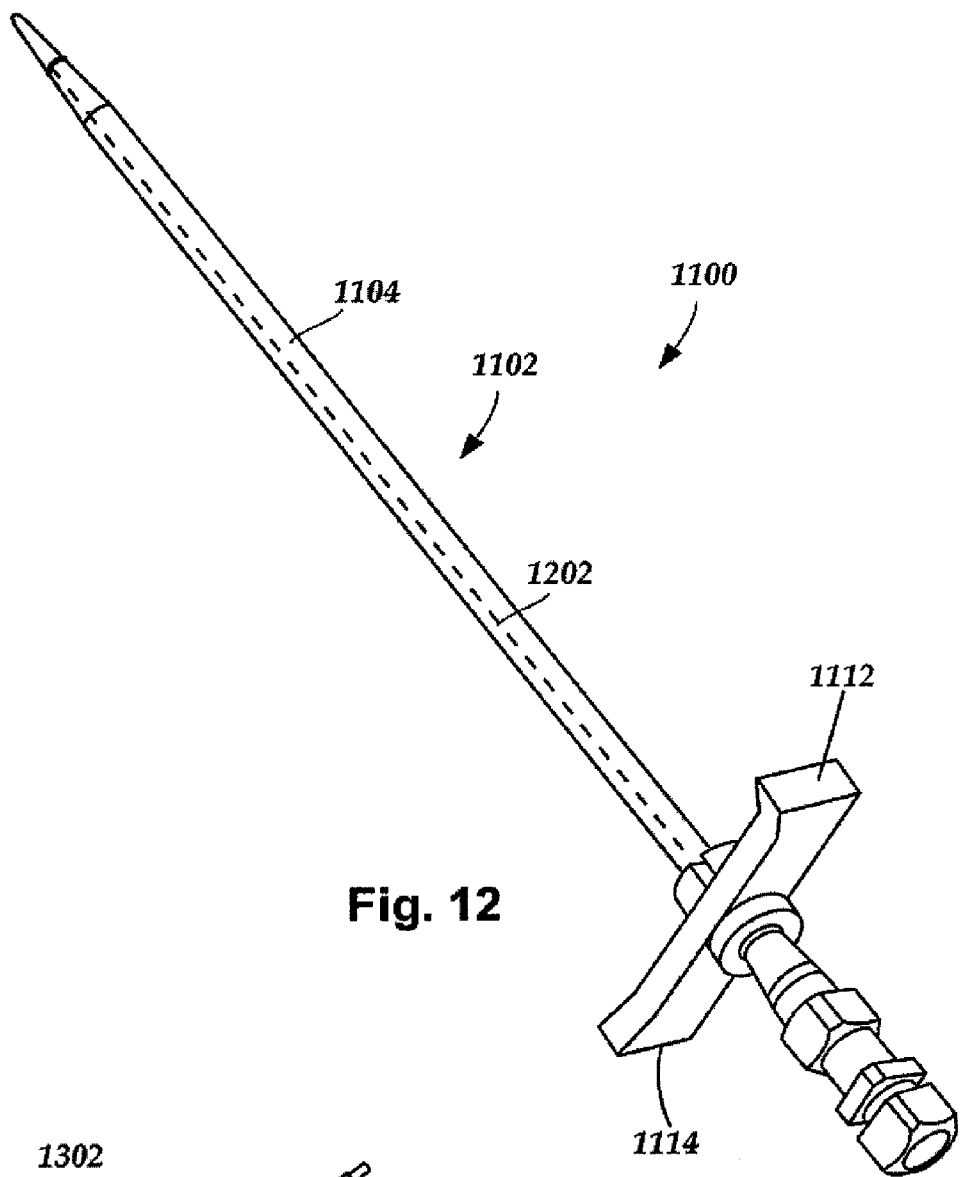
FIG. 12 is a schematic perspective view of one embodiment of the pull-apart implantation system shown in FIG. 11 with an obturator inserted into an insertion needle, according to the invention.

In at least some embodiments, at least a portion of the obturator 906 may be disposed within the cannula 1104. FIG. 12 is a schematic perspective view of one embodiment of the pull-apart implantation system 1100 with the obturator (906 in FIG. 10) disposed in the cannula 1104 of the insertion needle 1102. The cannula 1104 includes one or more weakened regions 1202, such as score lines or perforations, extending along at least a portion of the longitudinal length of the cannula 1104 from between the at least two pull-apart tabs 1112 and 1114. In at least some embodiments, when the at least two pull-apart tabs 1112 and 1114 are separated from one another, for example, by pulling each pull-apart tab away from the other pull-apart tab(s) in directions approximately orthogonal to the cannula 1104, the cannula 1104 separates along the one or more weakened regions 1202.

Figure 13:
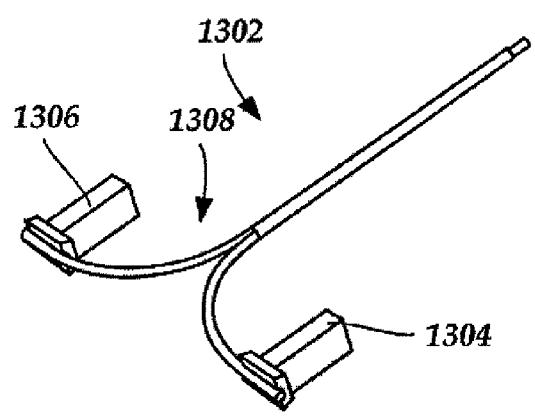
FIG. 13 is a schematic perspective view of one embodiment of a splitable member of a pull-apart implantation system, the splitable member being partially separated into two parts, according to the invention.

FIG. 13 is a schematic perspective view of one embodiment of a splitable member 1302 with pull-apart tabs 1304 and 1306 on opposite sides of a proximal end 1308 of the splitable member 1302 that have been separated from one another. In FIG. 13, the splitable member 1302 is shown separated along approximately one third of the longitudinal length of the splitable member 1302. In some embodiments, the splitable member 1302 is the introducer sheath 902. In other embodiments, the splitable member 1302 is the insertion needle 1102.

In at least some embodiments, implantation of an electrical stimulation system using the pull-apart implantation system 900 begins by nesting the insertion needle 904 and the obturator 906 into the body 912 of the introducer sheath 902, as shown in FIG. 10. The introducer sheath 902 is then guided to a desired location within a patient. Once in proximity to the desired location, the obturator 906 is removed. In some embodiments, fluid may then be introduced or removed through the luer fitting 928 to check for precise positioning of the introducer sheath 902, for example, in an epidural space of the patient.

Once the positioning of the introducer sheath 902 is confirmed, the distal end (see e.g., 706 of FIG. 7) of the lead (see e.g., 702 of FIG. 7) is then inserted into the body 912 of the introducer sheath 902. In at least some embodiments, the lead (see e.g., 702 of FIG. 7) is inserted into the body 912 of the introducer sheath 902 until the distal end (see e.g., 706 of FIG. 7) of the lead (see e.g., 702 of FIG. 7) is positioned at the desired location. In at least some embodiments, a stylet may be inserted into one or more lumens of the lead to facilitate insertion of the lead into the body 912 of the introducer sheath 902. In at least some embodiments, the lead is positioned with the aid of one or more types of medical imaging, such as fluoroscopy.

In at least some embodiments, implantation of an electrical stimulation system using the pull-apart implantation system 1100 begins by nesting the obturator 906 into the insertion needle 1102, as shown in FIG. 12. The insertion needle 1102 is then guided to a desired location within a patient. Once in proximity to the desired location, the obturator 906 is removed. In some embodiments, fluid may then be introduced or removed through the luer fitting 928 to check for precise positioning of the insertion needle 1102, for example, in an epidural space of the patient.

Once the positioning of the insertion needle 1102 is confirmed, the distal end (see e.g., 706 of FIG. 7) of the lead (see e.g., 702 of FIG. 7) is then inserted into the cannula 1104 of the insertion needle 1102. In at least some embodiments, the lead (see e.g., 702 of FIG. 7) is inserted into the cannula 1104 of the insertion needle 1102 until the distal end (see e.g., 706 of FIG. 7) of the lead (see e.g., 702 of FIG. 7) is positioned at the desired location. In at least some embodiments, a stylet may be inserted into one or more lumens of the lead to facilitate insertion of the lead into the cannula 1104. In at least some embodiments, the lead is positioned with the aid of one or more types of medical imaging, such as fluoroscopy.

Figure 14A:
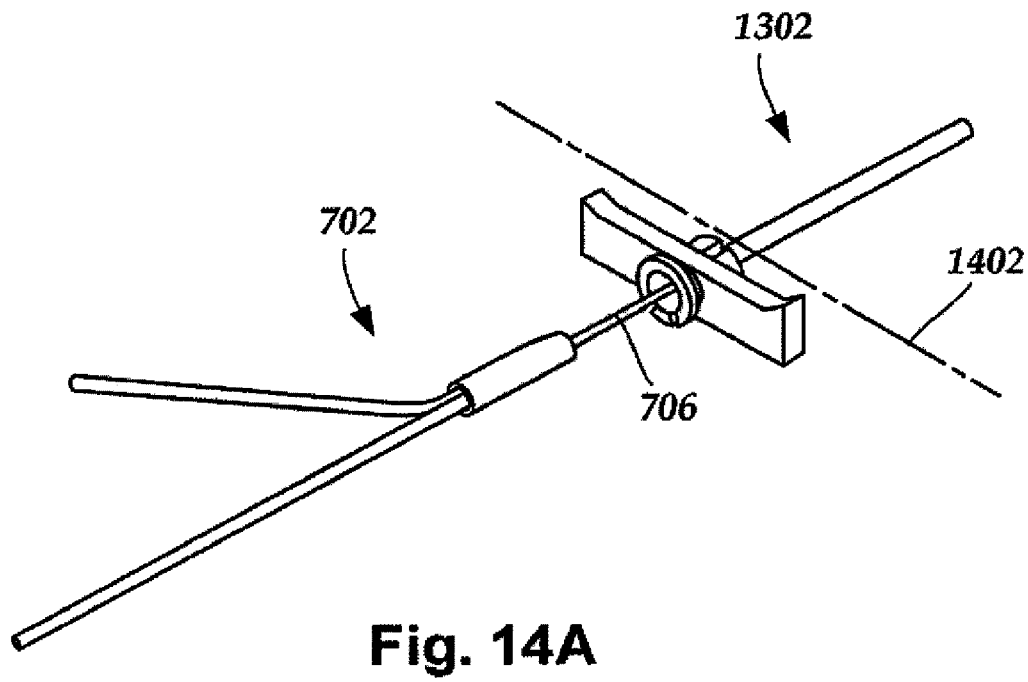
FIG. 14A is a schematic perspective view of one embodiment of the distal end of the lead shown in FIG. 8 disposed in the splitable member shown in FIG. 13 which, in turn, is disposed in a patient, according to the invention.

Once the splitable member 1302 (either the introducer sheath 902 of the pull-apart implantation system 900 or the insertion needle 1102 of the pull-apart implantation system 1100) is positioned and the lead (see e.g., 702 of FIG. 7) is inserted in the splitable member 1302, the splitable member 1302 is removed from the lead (see e.g., 702 of FIG. 7). FIG. 14A is a schematic perspective view of one embodiment of the distal end 706 of the lead 702 disposed in the splitable member 1302 which, in turn, is disposed in a patient, as shown by a line of alternating dashes and dots 1402. In at least some embodiments, the splitable member 1302 may be removed from the lead 702 by separating the splitable member 1302 along the one or more weakened regions (1002 in FIG. 10 or 1202 in FIG. 12) by separating the pull-apart tabs 1304 and 1306 from one another, as described above with reference to FIG. 13.

Figure 14B:
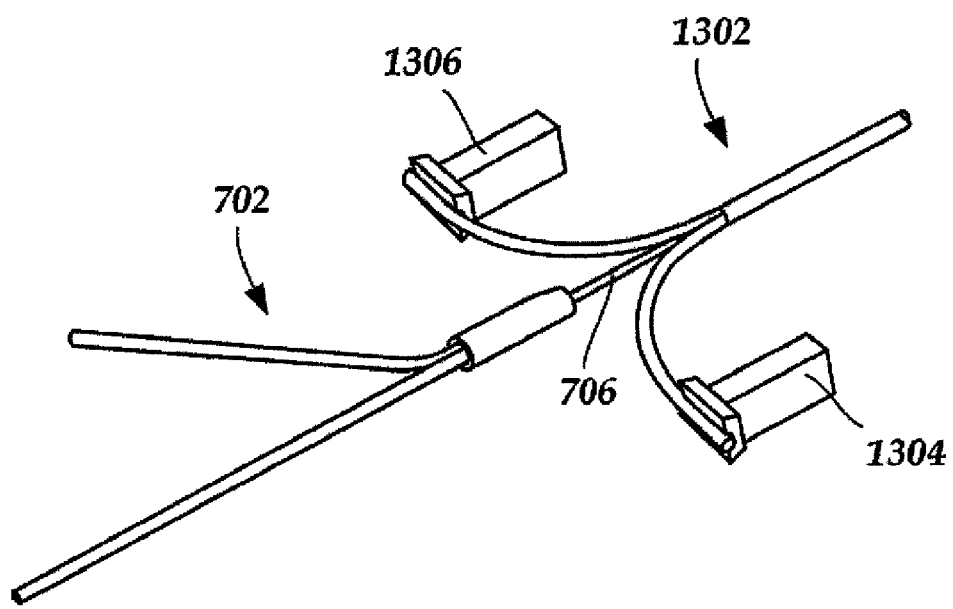
FIG. 14B is a schematic perspective view of one embodiment of the splitable member shown in FIG. 14A being separated from the lead shown in FIG. 14A along a longitudinal length of the splitable member, according to the invention.

FIG. 14B is a schematic perspective view of one embodiment of the splitable member 1302 being separated from the lead 702 by splitting the splitable member 1302 into a plurality of strips while pulling the splitable member 1302 proximally along the lead 702. As the splitable member 1302 splits apart, the distal end (see e.g., 908 of FIG. 9) of the splitable member 1302 moves proximally along the distal end 706 of the lead 702, with an increasing amount of the distal end 706 of the lead 702 extending through the open tip (see e.g., 918 of FIG. 9) of the splitable member 1302. Eventually, the splitable member 1302 may be completely separated into two or more longitudinal strips, thereby separating completely from the distal end 706 of the lead 702 and also from the patient. In at least some embodiments, the distal ends of the splitable member 1302 may be extracted from the patient as the splitable member 1302 is split apart. In at least some embodiments, the splitable member may be split apart without causing the lead 702 to move.

Once the splitable member 1302 is separated from the distal end 706 of the lead 702, the proximal ends of the lead 706 can be coupled to a control module and implanted using well-known techniques, for example, using one or more using tunneling straws placed in passageways underneath patient skin with bores that are sized large enough to receive a junction and the proximal ends of the lead. In one embodiment, one or more tunneling straws each have an inner diameter of 0.18 inches (0.46 cm). In at least some embodiments, the proximal ends of a lead can be coupled to a connector of a control module, as shown in FIG. 3. In other embodiments, one or more of the proximal ends can be coupled to one or more other devices, including an adaptor, a lead extension, an operating room cable, or the like or combinations thereof.

Figure 15:
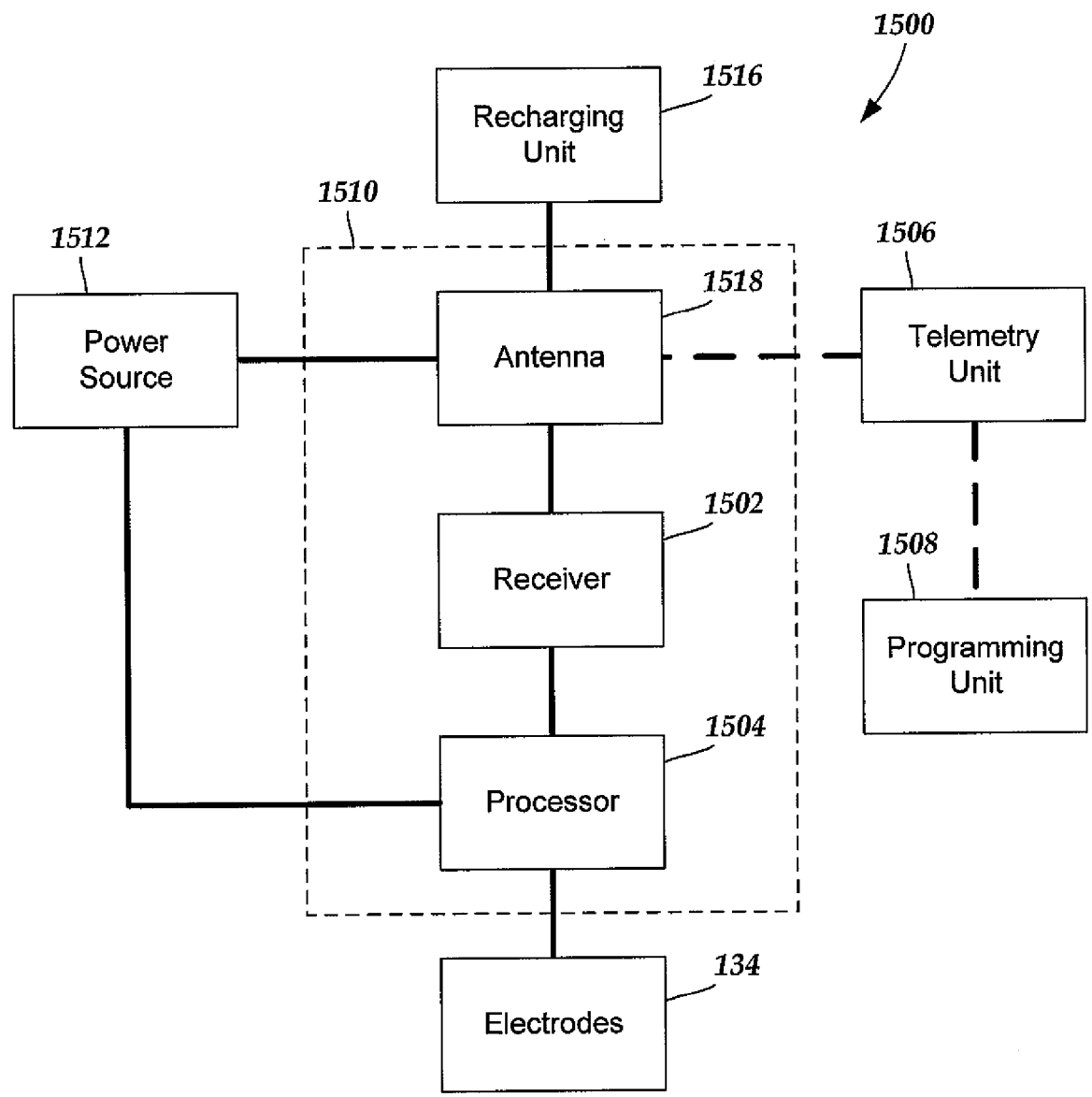
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An insertion kit comprising:
   a neurostimulation lead with a distal end and at least two proximal ends, the neurostimulation lead comprising
      a plurality of electrodes disposed at the distal end,
      a plurality of terminals disposed at the proximal ends,
      a plurality of conductive wires coupling the plurality of electrodes electrically to the plurality of terminals, and
      a junction coupling the distal end of the neurostimulation lead to the proximal ends of the neurostimulation lead;
   a splitable member configured and arranged for receiving the neurostimulation lead when implanting the neurostimulation lead into a patient, wherein the splitable member defines a lumen for receiving the distal end of the neurostimulation lead, wherein the splitable member is configured and arranged to divide into at least two parts for removal of the splitable member from the neurostimulation lead upon implantation of the neurostimulation lead into the patient; and
   an insertion needle configured and arranged for insertion into the lumen of the splitable member.

2. The insertion kit of claim 1, wherein the splitable member comprises an introducer sheath.

3. The insertion kit of claim 1, wherein the splitable member has a proximal end and a distal end, the splitable member comprising at least two pull-apart tabs disposed at opposite sides of the proximal end.

4. The insertion kit of claim 3, wherein the splitable member further comprises
   a body extending from the distal end to the at least two pull-apart tabs; and
   at least one weakened region extending along at least a portion of a longitudinal length of the body of the splitable member from between the at least two pull-apart tabs, the at least one weakened region configured and arranged for separating when the at least two pull-apart tabs are pulled apart from one another in directions approximately orthogonal to the body of the splitable member.

5. The insertion kit of claim 4, wherein the at least one weakened region comprises at least one of a score line or a line of perforations.

6. The insertion kit of claim 1, further comprising an obturator configured and arranged for disposing in the splitable member.

7. The insertion kit of claim 1, wherein the neurostimulation lead defines a plurality of lumens, the plurality of lumens defined by the neurostimulation lead comprising a central lumen and a plurality of outer lumens.

8. The insertion kit of claim 7, wherein the plurality of conductive wires are disposed in the plurality of outer lumens.

9. The insertion kit of claim 7, wherein at least two conductive wires are disposed in each of the plurality of outer lumens.

10. An electrical stimulating system comprising:
    the insertion kit of claim 1;
    a control module configured and arranged to electrically couple to the first proximal end and the at least one second proximal end, the control module comprising
       a housing, and
       an electronic subassembly disposed in the housing; and
    a connector for receiving the neurostimulation lead, the connector comprising
       a connector housing defining a first port for receiving the first proximal end and at least one second port for receiving the at least one second proximal end of the neurostimulation lead, and
       a plurality of connector contacts disposed in the connector housing, the connector contacts configured and arranged to couple to at least one first terminal disposed at the first proximal end of the neurostimulation lead and to at least one second terminal disposed at each of the at the at least one second proximal ends.

11. A neurostimulation lead comprising:
    a distal lead body having a distal end and a proximal end, the distal lead body comprising
       a plurality of electrodes disposed on the distal end,
       a plurality of conductive wires extending from the electrodes to the proximal end, and
       a plurality of lumens extending from the electrodes to the proximal end, each of the plurality of lumens configured and arranged for receiving a plurality of the conductive wires;
    at least two proximal lead bodies having a distal end and a proximal end, the at least two proximal lead bodies each comprising
       a plurality of terminals disposed on the proximal end,
       a plurality of conductive wires extending from the terminals to the distal end, and
       a plurality of lumens extending from the terminals to the distal end, each of the plurality of lumens configured and arranged for receiving a single conductive wire; and
    a junction coupling the proximal end of the distal lead body to the distal ends of each of the proximal lead bodies, wherein each of the conductive wires extending from the electrodes electrically couples to at least one conductive wire extending from at least one of the terminals disposed on at least one of the proximal lead bodies.

12. A neurostimulation lead of claim 11, wherein the total number of terminals disposed on each of the proximal lead bodies is equal to the number of electrodes disposed on the distal lead body.

13. A neurostimulation lead of claim 11, wherein there is an equal number of terminals disposed on each of the proximal lead bodies.

14. The neurostimulation lead of claim 11, wherein each of the plurality of lumens defined in the distal lead body is configured and arranged to receive two conductive wires of the plurality of conductive wires.

15. The neurostimulation lead of claim 11, wherein the distal lead body has a lateral circumference that is no greater than a lateral circumference of either of the at least two proximal lead bodies.

16. The neurostimulation lead of claim 11, wherein the at least two proximal lead bodies comprises a first proximal lead body and a second proximal lead body, and wherein the number of conductive wires disposed in the first proximal lead body is equal to number of conductive wires disposed in the second proximal lead body.

17. A method for implanting a neurostimulation lead into a patient, the method comprising:
    inserting an obturator into an insertion needle;
    inserting the insertion needle into a splitable member, the splitable member defining a lumen for receiving the obturator;
    guiding the splitable member with the obturator to a desired location within the patient;
    removing the obturator, leaving the splitable member in the patient;

inserting into the lumen of the splitable member a distal end of a neurostimulation lead, the neurostimulation lead comprising a plurality of electrodes disposed along the distal end of the neurostimulation lead and a plurality of terminals disposed along at least one proximal end of the neurostimulation lead;

separating the splitable member into at least two parts along the length of the lumen; and removing the splitable member from the neurostimulation lead, leaving at least the distal end of the neurostimulation lead implanted in the patient.

18. The method of claim 17, wherein the neurostimulation lead comprises at least two proximal ends and further comprises a junction coupling the distal end of the neurostimulation lead to the at least two proximal ends.

19. The method of claim 18, wherein separating the splitable member into at least two parts along the length of the lumen to remove the splitable member from the neurostimulation lead comprises separating the splitable member into at least two parts along the length of the lumen to remove the splitable member from a portion of the neurostimulation lead distal to the junction.

20. The method of claim 18, wherein inserting into the lumen of the splitable member the distal end of the neurostimulation lead comprises inserting a stylet into a lumen defined in the distal end of the neurostimulation lead and inserting into the lumen of the splitable member the distal end of the neurostimulation lead with the stylet.

* * * * *